United States Patent
Dammann

(10) Patent No.: US 7,987,848 B2
(45) Date of Patent: Aug. 2, 2011

(54) SYSTEM AND METHOD OF INTEGRATING ANESTHESIA AGENT MONITORING IN A RESPIRATORY CARESTATION

(75) Inventor: Bruce Dammann, Middleton, WI (US)

(73) Assignee: General Electric Company, Schenectady, NY (US)

( * ) Notice: Subject to any disclaimer, the term of this patent is extended or adjusted under 35 U.S.C. 154(b) by 1036 days.

(21) Appl. No.: 11/270,267

(22) Filed: Nov. 9, 2005

(65) Prior Publication Data

US 2007/0101993 A1  May 10, 2007

(51) Int. Cl.
*A61M 16/00* (2006.01)
*A61M 16/01* (2006.01)
*A61M 16/18* (2006.01)

(52) U.S. Cl. ......... 128/204.23; 128/200.24; 128/202.27; 128/203.12; 128/204.18; 128/204.21; 128/204.22; 128/204.26

(58) Field of Classification Search ............. 128/203.12, 128/203.13, 204.23; 600/529, 530, 531
See application file for complete search history.

(56) References Cited

U.S. PATENT DOCUMENTS

| | | | |
|---|---|---|---|
| 3,831,599 A | | 8/1974 | Needham |
| 5,687,717 A * | | 11/1997 | Halpern et al. ................ 600/300 |
| 5,957,838 A * | | 9/1999 | Rantala ........................ 600/300 |
| 6,158,430 A * | | 12/2000 | Pfeiffer et al. ........... 128/202.27 |
| 6,325,978 B1 * | | 12/2001 | Labuda et al. .................. 422/84 |
| 6,551,243 B2 * | | 4/2003 | Bocionek et al. ............. 600/300 |
| 6,571,792 B1 * | | 6/2003 | Hendrickson et al. .... 128/203.12 |
| 6,782,888 B1 * | | 8/2004 | Friberg et al. ............ 128/204.18 |
| 7,455,062 B2 * | | 11/2008 | Roehl et al. .............. 128/204.21 |
| 2002/0189609 A1 * | | 12/2002 | Stromberg ................ 128/200.14 |
| 2005/0005932 A1 * | | 1/2005 | Berman .................... 128/203.12 |
| 2005/0056283 A1 | | 3/2005 | Levi et al. ................ 128/204.21 |
| 2005/0124866 A1 * | | 6/2005 | Elaz et al. ..................... 600/301 |
| 2005/0133027 A1 | | 6/2005 | Elaz et al. |
| 2006/0201503 A1 * | | 9/2006 | Breen ....................... 128/204.18 |
| 2007/0034208 A1 * | | 2/2007 | Roehl et al. .............. 128/204.23 |

FOREIGN PATENT DOCUMENTS

EP  0 919 253 A2  6/1999
WO  WO 2004032727 A2 *  4/2004

OTHER PUBLICATIONS

Anonymous: "510(k) Summary of Safety and Effectiveness Information for the GE Datex-Ohmeda Engstrom Carestation", Internet Article, Sep. 27, 2005, K051895, entire document.*
Hugo et al., Notfall-und Intensivmedizin, Jan. 2005, p. 67, second column, discloses an Engstrom Carestation.*
FDA U.S. Food and Drug Administration, 510(k) Clearances, Sep. 7, 2010, pp. 1-2.*

(Continued)

*Primary Examiner* — Justine Yu
*Assistant Examiner* — Clinton T Ostrup
(74) *Attorney, Agent, or Firm* — Andrus, Sceales, Starke & Sawall, LLP

(57) ABSTRACT

The present invention is a system and method for integrating anesthesia agent monitoring in a respiratory carestation, wherein the respiratory carestation is configured to be compatible with a variety of monitoring modules. Any one of the monitoring modules is inserted into a module bay, and a sampling line couples the monitoring module to the patient circuit, such that the patient monitoring parameters are displayed on a user interface of the respiratory carestation.

6 Claims, 2 Drawing Sheets

OTHER PUBLICATIONS

Mathews et al., Focus Journal, Sep./Oct. 2007, University of Kansas Equipment Reviews, The Engstrom Carestation Critical Care Ventilator, pp. 52-53, second full paragraph on p. 52.*

Anonymous: "510(k) Summary of Safety and Effectiveness Information for the GE Datex-Ohmeda Engstrom Carestation", Internet Article, Mar. 25, 2005, XP002421161.

Anonymous: "510(k) Summary of Safety and Effectiveness Information for the GE Datex-Ohmeda Engstrom Carestation", Internet Article, Nov. 24, 2004, XP002421162.

European Search Report dated Mar. 16, 2007.

* cited by examiner

SYSTEM AND METHOD OF INTEGRATING ANESTHESIA AGENT MONITORING IN A RESPIRATORY CARESTATION

FIELD OF THE INVENTION

The invention relates to the field respiratory carestations. More specifically, the invention relates to the field of integrating gas monitoring with respiratory carestations.

BACKGROUND OF THE INVENTION

The need and desire to use volatile anesthetic agents on patients in intensive care units (ICU) has existed ever since these drugs became available. Presently, these anesthetic agents are primarily used in the operating room (OR) and have had minimal use within the ICU. This limited use is due to the technical issues regarding the use of anesthesia delivery systems, proper disposal of waste gas, and the need for specific agent monitoring that is not readily available outside the OR.

Current anesthetic delivery devices provide a simplified means of delivering volatile anesthetic agents to ICU patients using a critical care ventilator. However, these new devices do not provide any monitoring capability, which is of the utmost importance when this device is used. Since anesthetic monitoring is not a typical modality available in most ICUs, it can be problematic for the clinicians to easily provide this type of monitoring. If the clinicians were able to have access to an anesthetic monitoring device, they would then have to be able to set it up within the ICU environment and understand the use and control of the device.

SUMMARY OF THE INVENTION

The present invention is a system and method for integrating anesthesia agent monitoring in a respiratory carestation, wherein the respiratory carestation is configured to be compatible with a variety of monitoring modules. Any one of the monitoring modules is inserted into a module bay, and a sampling line couples the monitoring module to the patient circuit, such that the patient monitoring parameters are displayed on a user interface of the respiratory carestation.

In one aspect of the present invention, an integrated system for anesthesia agent monitoring comprises a ventilator, the ventilator including a module bay and a display, a patient circuit configured to couple a patient with the ventilator and a monitoring module coupled to the patient circuit and configured for insertion into the ventilator, such that a set of patient monitoring parameters detected by the monitoring module are displayed on the display. The system further comprises a sampling line, wherein the sampling line couples the monitoring module with the patient circuit, and a respiratory carestation, wherein the respiratory carestation includes the ventilator, a user interface including the display, and the module bay. The monitoring module corresponds to an anesthetic agent, and the ventilator is further configured with a plurality of module bays, such that a plurality of monitoring modules may be inserted simultaneously.

In another aspect of the present invention, a method of integrating a respiratory carestation with a monitoring module comprises configuring the respiratory carestation with a module bay such that the respiratory carestation is compatible with the monitoring module, inserting the monitoring module into the module bay, coupling the monitoring module to a patient circuit with a sampling line, monitoring the patient circuit for volatile anesthetic agents, and displaying a set of patient parameters on a user interface of the respiratory carestation. The monitoring module corresponds to an anesthetic agent, and the method further comprises configuring the respiratory carestation with a plurality of module bays, such that a plurality of monitoring modules may be inserted simultaneously.

In yet another aspect of the present invention, a system for anesthesia agent monitoring comprises a respiratory carestation including a ventilator, a user interface having a display and a module bay, as well as a patient circuit configured to couple a patient with the respiratory carestation, a monitoring module configured for insertion into the ventilator, and a sampling line configured to couple the monitoring module to the patient circuit wherein a set of patient monitoring parameters detected by the monitoring modules are displayed on the display.

DETAILED DESCRIPTION OF THE INVENTION

The present invention provides the ability to integrate patient monitoring parameters directly into a critical care ventilator by utilizing monitoring modules that are compatible with the ventilator carestation, and vice versa. By inserting a monitoring module that provides anesthetic agent analysis, into the ventilator's module bay, and connecting a sampling line to a patient circuit, the monitoring module will provide analysis of the patient gas composition including the type and concentration of the anesthetic agent that is present. This data is then displayed on the ventilator's use interface, providing both numeric and graphical representations. The ability of integrating agent monitoring eliminates the clinician's problem of finding, setting up and using a separate anesthetic monitor in the ICU environment.

This "Plug & Play" capability of the integrated carestation of the present invention allows a user to insert a monitoring module and have the ventilator immediately recognize the module and begin displaying the data. This allows the user to easily move this monitoring capability from ventilator to ventilator as the need arises without having to move large, bulky equipment around the ICU.

Figure 1:
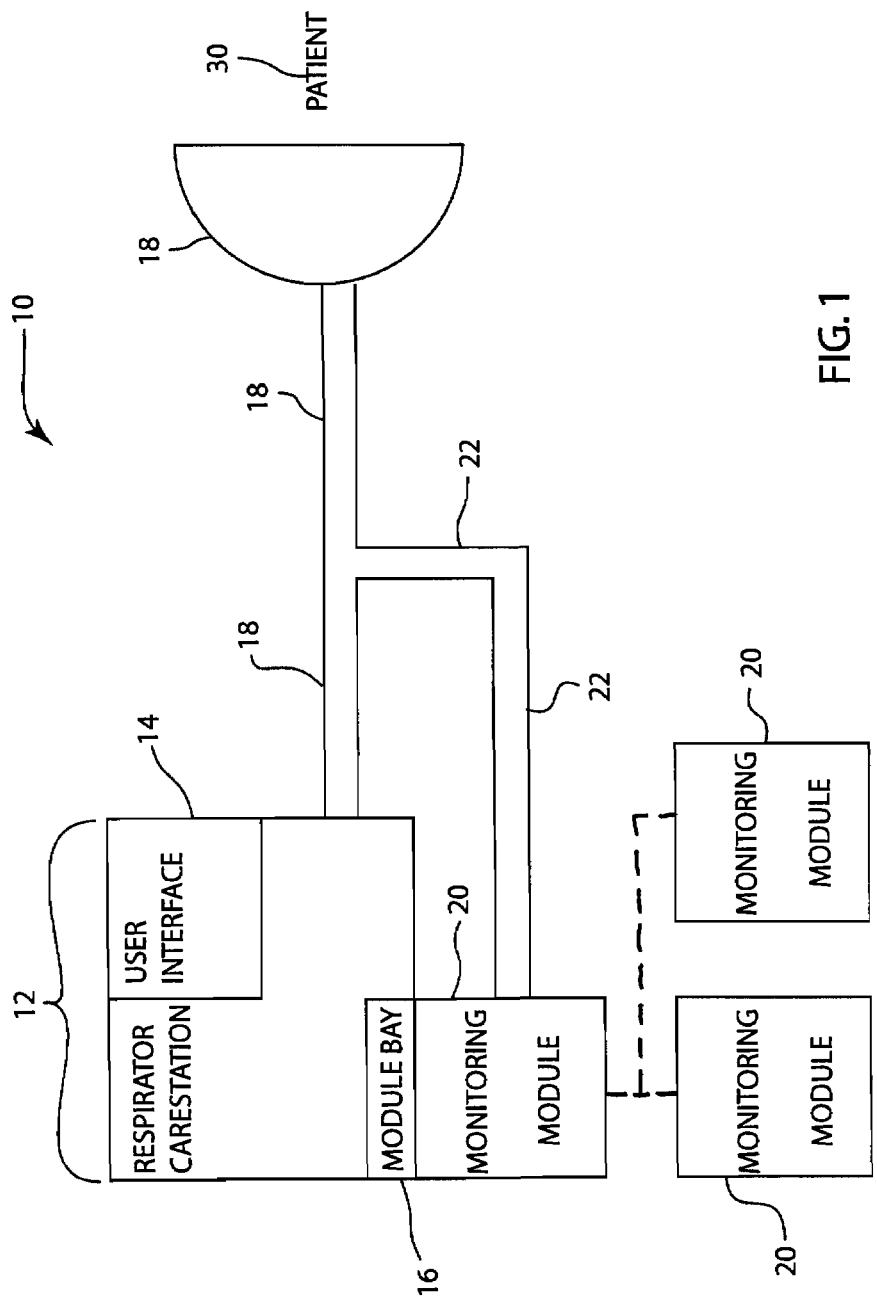
FIG. 1 illustrates a block diagram according to an embodiment of the system of the present invention.

Referring now to FIG. 1, an embodiment of the system of the present invention is illustrated. The integrated system 10 includes a respiratory carestation 12. The respiratory carestation 12 preferably includes a user interface 14 and at least one module bay 16. The user interface 14 preferably includes a display, as well as user controls for operating the respiratory carestation 12. The respiratory carestation is configured to be made compatible with gas monitoring modules 20, such that the monitoring modules 20 can be inserted into the module bay 16, and provide gas monitoring that is displayed on the display of the user interface 14. Preferably, the respiratory carestation 12 includes a number of module bays 16 (not shown), configured to be able to accommodate more then one monitoring module 20.

Still referring to FIG. 1, the respiratory carestation 12 of the present invention is preferably the Engstrom Carestation™, manufactured and distributed by GE Healthcare. However, any respiratory carestation 12 that is configured to be compatible with the gas monitoring modules 20 by installing a module bay 16, may be utilized. The monitoring modules 20 are preferably Compact Airway modules, M series, also manufactured and distributed by GE Healthcare, having the product names M-CAiO, M-CAiOV or M-CAiOVX, or alternatively, the E-series monitoring modules manufactured by GE Healthcare having the product names E-CAiO, E-CAiOV or E-CAiOVX. However, any monitoring modules capable of compatibility with the respiratory carestation 12 may be utilized.

Referring again to FIG. 1, the ventilator of the respiratory carestation 12 provides ventilation to the patient 30 through the patient circuit 18. A sampling line 22 samples the gas traveling through the patient circuit 18 and carries that gas to the monitoring module 20 for analysis. The sampling line 22 may be configured to sample gas in the patient circuit 18 at any point desirable by the user. For example, the sampling line may sample gas from the patient circuit 18 on an end near the patient 30, or closer to the carestation 12. Furthermore, various monitoring modules 20 may be used according to the types of gas a user would like to detect and the number of gases a user desires to detect. The monitoring modules 20 that have the anesthetic monitoring capability, designated by the "Ai" above, are capable of detecting and measuring any of the volatile agents currently in use: Halothane; Isoflurane; Enflurane; Sevoflurane; and Desflurane, as well as nitrous oxide and mixtures of all of these agents. When these particular monitoring modules 20 are in use, there is no need to change out monitoring modules 20 in order to monitor any of these anesthetic agents.

Figure 2:
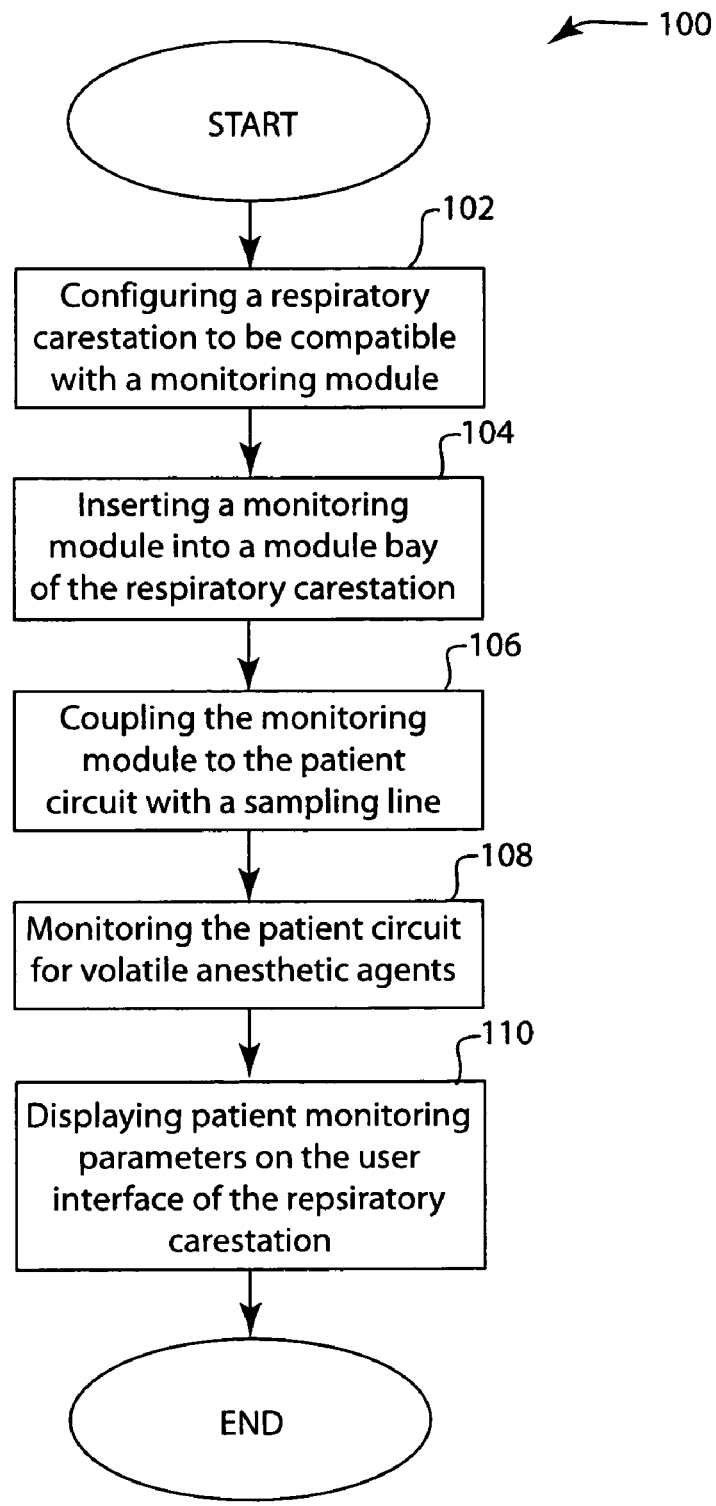
FIG. 2 illustrates a flow chart according to an embodiment of the method of the present invention.

Referring now to FIG. 2, an integrating method 100 of the present invention is depicted in the flow chart. In step 102, a respiratory carestation is configured with the module bay to be compatible with a monitoring module. In step 104, a monitoring module is inserted in the module bay of the respiratory carestation. In step 106 the monitoring module is coupled to a patient circuit with a sampling line, and in step 108 the patient circuit is monitored for volatile anesthetic agents, as desired by the user. In step 110, patient monitoring parameters are displayed on the user interface of the respiratory carestation, according to the monitoring step 108.

The present invention provides a system and method of analyzing gas delivery for halogenated hydro-carbons (volatile agents) in an ICU and/or transport setting; a new application area (ICU and transport) for the anesthetic agent monitoring modules; an improved ease of use for clinicians who need to monitor anesthetic agent delivery within the ICU environment; increased cost savings by allowing the hospital to use their existing technology (Compact Airway modules) in a broader application arena; and continuous documentation of anesthetic agent delivery via connection with information management system.

The present invention provides an integration of monitoring modalities, like anesthesia agent analysis, into a critical care ventilator. Current critical care ventilators do not have this capability at this time. In order to display volatile agent analysis, the end user must either utilize a separate monitor that measures and displays agent concentration or utilize an anesthesia monitor with a gas bench. Having the capability to accept monitoring modules, that are used in a current patient monitoring platform, is unique in that the modules can be moved from a monitor and placed within the ventilator providing the same measured and calculated parameters. Furthermore, the present invention provides consistency of measured data that users are familiar with from the OR setting to the ICU setting.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

I claim:

1. An integrated system for anesthesia agent monitoring, the system comprising:
   a ventilator, the ventilator including a module bay and a display;
   a patient circuit configured to couple a patient with the ventilator; and
   a monitoring module configured to detect a corresponding anesthetic, the monitoring module including a carestation interface and a sampling line interface such that the monitoring module is coupled to the patient circuit and removably coupled with the module bay of the ventilator, wherein the ventilator recognizes the monitoring module, and further wherein the monitoring module detects a set of patient monitoring parameters including a level of the corresponding anesthetic, such that the set of patient monitoring parameters and the anesthetic detected by the monitoring module are displayed on the display,
   wherein the ventilator is further configured with a plurality of module bays, such that a plurality of monitoring modules may be inserted simultaneously.

2. The system as claimed in claim 1, further comprising a sampling line, wherein the sampling line couples the monitoring module with the patient circuit.

3. The system as claimed in claim 1, further comprising a respiratory carestation, wherein the respiratory carestation includes:
   the ventilator;
   a user interface including the display; and
   the module bay.

4. A method of integrating a respiratory carestation with a monitoring module, the method comprising:
   configuring the respiratory carestation with a plurality of module bays, such that the respiratory carestation is compatible with the monitoring module and further such that a plurality of monitoring modules may be inserted simultaneously, wherein the monitoring module includes a carestation interface and a sampling line interface;
   inserting the monitoring module into one of the plurality of module bays with the carestation interface;
   the ventilator recognizing the inserted monitoring module;
   coupling the monitoring module configured to detect a volatile anesthetic agent to a patient circuit with the sampling line interface;
   monitoring the patient circuit for the volatile anesthetic agent; and
   displaying a set of detected patient parameters including the volatile anesthetic agent on a user interface of the respiratory carestation.

5. The method as claimed in claim 4, wherein the monitoring module corresponds to the volatile anesthetic agent.

6. A system for anesthesia agent monitoring, the system comprising:
   a respiratory carestation including:
      a ventilator;
      a user interface having a display; and
      a module bay;
   a patient circuit configured to couple a patient with the respiratory carestation;

a monitoring module including a carestation interface and a sampling line interface, configured to detect a corresponding anesthetic, the monitoring module removably inserted into the ventilator and recognized by the ventilator, wherein the monitoring module detects a set of patient monitoring parameters including a level of the anesthetic agent; and a sampling line configured to couple the monitoring module to the patient circuit, wherein the set of patient monitoring parameters and the level of the anesthetic agent detected by the monitoring modules are displayed on the display, wherein the ventilator is further configured with a plurality of module bays, such that a plurality of monitoring modules may be inserted simultaneously.

* * * * *